(12) United States Patent
Schueren et al.

(10) Patent No.: US 12,141,884 B2
(45) Date of Patent: *Nov. 12, 2024

(54) CROWD-SOURCED AUTOMATED REVIEW OF FORENSIC FILES

(71) Applicant: IntegenX Inc., Pleasanton, CA (US)

(72) Inventors: Robert A. Schueren, Los Altos Hills, CA (US); David King, Menlo Park, CA (US); Stevan B. Jovanovich, Livermore, CA (US)

(73) Assignee: INTEGENX, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/500,690

(22) Filed: Oct. 13, 2021

(65) Prior Publication Data

US 2022/0053592 A1 Feb. 17, 2022

Related U.S. Application Data

(62) Division of application No. 15/570,730, filed as application No. PCT/US2016/030331 on Apr. 30, 2016, now Pat. No. 11,151,674.

(Continued)

(51) Int. Cl.
*G01N 33/48* (2006.01)
*G01N 33/50* (2006.01)
(Continued)

(52) U.S. Cl.
CPC ........... *G06Q 50/26* (2013.01); *G06F 16/116* (2019.01); *G06Q 10/06311* (2013.01); *G06Q 10/063112* (2013.01); *G06Q 30/0611* (2013.01); *G06Q 50/01* (2013.01); *G06Q 50/18* (2013.01); *G16B 50/00* (2019.02); *H04W 36/305* (2018.08); *H04W 56/001* (2013.01);
(Continued)

(58) Field of Classification Search
CPC ................................ G06Q 50/01; G16B 50/00
See application file for complete search history.

(56) References Cited

U.S. PATENT DOCUMENTS 8,894,946 B2 11/2014 Nielsen et al.
11,151,674 B2 * 10/2021 Schueren .............. G06F 16/116
(Continued)

FOREIGN PATENT DOCUMENTS

| CN | 102279947 A | 12/2011 |
|---|---|---|
| CN | 102812460 A | 12/2012 |
| CN | 104573995 A | 4/2015 |

OTHER PUBLICATIONS

International Search Report and Written Opinion dated Oct. 28, 2016, issued in PCT Application No. PCT/US16/30331, filed Apr. 30, 2016.

(Continued)

*Primary Examiner* — Russell S Negin
(74) *Attorney, Agent, or Firm* — JONES ROBB, PLLC

(57) ABSTRACT

Provided herein is a system and method for review of forensic report computer files. The method can involve notifying a plurality of service providers of a job to be performed, accepting a bid from a service provider to perform the job, providing the computer file to the service provider, receiving from the service provider a forensic result such as a reviewed file.

17 Claims, 15 Drawing Sheets

Related U.S. Application Data

(60) Provisional application No. 62/155,400, filed on Apr. 30, 2015.

(51) Int. Cl.

| | |
|---|---|
| *G06F 16/11* | (2019.01) |
| *G06Q 10/0631* | (2023.01) |
| *G06Q 30/0601* | (2023.01) |
| *G06Q 50/00* | (2012.01) |
| *G06Q 50/18* | (2012.01) |
| *G06Q 50/26* | (2012.01) |
| *G16B 50/00* | (2019.01) |
| *H04W 36/30* | (2009.01) |
| *H04W 56/00* | (2009.01) |
| *H04W 72/21* | (2023.01) |
| *H04W 76/19* | (2018.01) |
| *H04W 76/27* | (2018.01) |
| *H04W 4/12* | (2009.01) |

(52) U.S. Cl.
CPC ....... *H04W 56/0045* (2013.01); *H04W 72/21* (2023.01); *H04W 76/19* (2018.02); *H04W 76/27* (2018.02); *H04W 4/12* (2013.01)

(56) References Cited

U.S. PATENT DOCUMENTS

| | | | |
|---|---|---|---|
| 2004/0151349 | A1 | 8/2004 | Milne, III et al. |
| 2008/0108057 | A1 | 5/2008 | Griffith |
| 2009/0275038 | A1 | 11/2009 | Hodge |
| 2011/0246326 | A1 | 11/2011 | Thomas |
| 2013/0115607 | A1 | 5/2013 | Nielsen et al. |
| 2013/0131994 | A1 | 5/2013 | Birdwell et al. |
| 2013/0202182 | A1 | 8/2013 | Rowe |
| 2014/0317681 | A1 | 10/2014 | Shende |
| 2015/0078552 | A1 | 3/2015 | Perlin |
| 2015/0088772 | A1 | 3/2015 | Shwartz et al. |

OTHER PUBLICATIONS

International Preliminary Report on Patentability dated Nov. 9, 2017, issued in PCT Application No. PCT/US16/30331, filed Apr. 30, 2016.

Wikipedia: "Mobile Web", Internet Article, Mar. 27, 2015 (Mar. 27, 2015), XP055497568, Retrieved from the Internet: URL:https://en.wikipedia.org/w/index.php?title=Mobile_Web&oldid=653815098 [retrieved on Aug. 6, 2018] , pp. 1-5 5.

Wikipedia: "Unified communications", Internet Article, ,Apr. 16, 2015 (Apr. 16, 2015), XP055497572, Retrieved from the Internet: URL:https://en.wikipedia.org/w/index.php?title=Unifiedcommunications&oldid=656726520, [retrieved on Aug. 6, 2018], pp. 1-5.

Wikipedia: "Extract, transform, load", Internet Article, Apr. 25, 2015 (Apr. 25, 2015), XP055497574, Retrieved from the Internet: URL:https://en.wikipedia.org/w/index.php?title=Extract,_transform,_load&oldid=659213002 [retrieved on Aug. 6, 2018], pp. 2.

Integenx: "IntegenX Announces First State-Wide deployment of the RapidHIT System with SmallPond(TM) at Arizona Department of Public Safety [ IntegenX Rapid DNA | DNA Fingerprinting", Internet Article, May 14, 2014 (May 14, 2014), XP055497550, pp. 10.

Vince Figarelli: "The Arizona DPS Rapid DNA Program", Intern et Article, Aug. 31, 2014 (Aug. 31, 2014), XP055497564, pp. 46.

Applied Biosystems: *GeneMapper Software Version 4.1— Reference and Troubleshooting Guide*, Internet Article, Apr. 14, 2009, XP055576713, retrieved from the Internet: URS:http://tools.thermofisher.com/content/sfs/manuals/ cms_070162.pdf [retrieved on Apr. 2, 2019].

Hennessy et al., *Developmental Validation of the Global Filer TM Express Kit, a 24-Marker STR Assay, on the RapidHIT TIM System*, forensic Science International: Genetics, Elsevier BV, Netherlands, vol. 13, Aug. 29, 2014, pp. 247-258.

John M. Butler, *Advanced Topis in Forensic DNA Typing: Interpretation*, Oct. 22, 2014, Academic Press, XP055576682, ISBN: 978-0-12-405213-0, pp. ToC, 3-39-47-51.

Larue et al., *An Evaluation of the RaidHIT TIM EPO Form 3906 01.91TRI System for Reliably Genotyping Reference Samples*, Forensic Science International: Genetics, Elsevier BV, Netherlands, vol. 13, Jul. 18, 2014, pp. 104-111.

Vermatt: *Discovering Computer: Essentials (Shelly Cashman)*, 1$^{st}$ Edition, Mar. 4, 2013, Course Technology, XP055302032, ISBN: 978-1-285-16178-5.

Search Report received for Chinese Patent Application No. 201680035497.8, dated Mar. 26, 2019, 2 pages. (reference provided in parent U.S. Appl. No. 15/570,730).

Second Office Action received for Chinese Patent Application No. 201680035497.8, dated Jan. 19, 2020, 10 pages (6 pages of English Translation and 4 pages of Original Document. (reference provided in parent U.S. Appl. No. 15/570,730).

Supplementary Search Report received for Chinese Patent Application No. 201680035497.8, dated Jan. 9, 2020, 1 page. (reference provided in parent U.S. Appl. No. 15/570,730).

Extended European Search Report dated Aug. 16, 2018 issued in Application No. EP 16787296.9. (reference provided in parent U.S. Appl. No. 15/570,730).

* cited by examiner

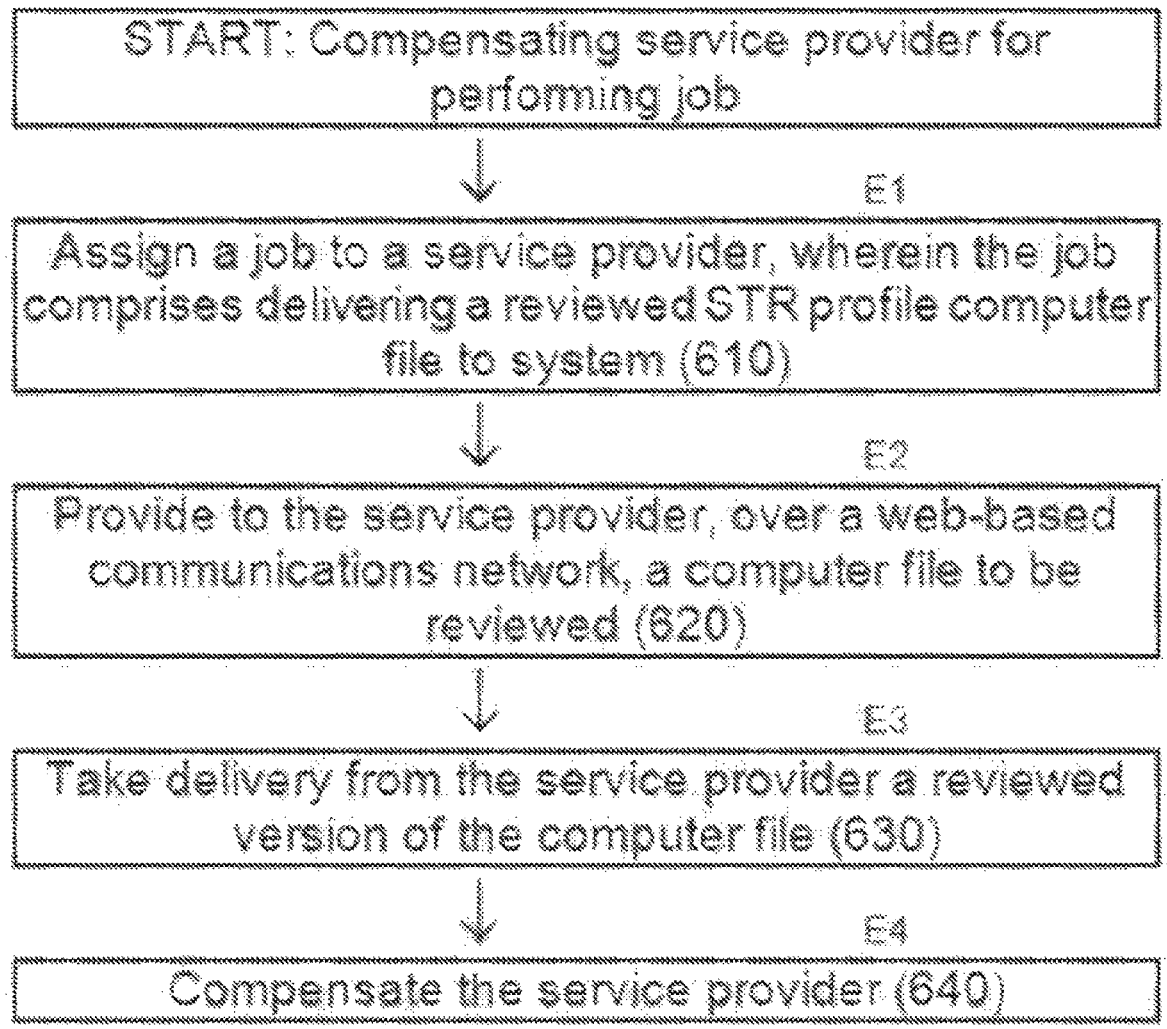

START: Bidding on crowd-sourced file review job by service provider

F1

Receive from system notification of a job to be performed, the job involving reviewing an STR profile computer file (710)

F2

Transmit to system, indication of willingness to accept job (720)

F3

Receive from system an STR profile computer file to be reviewed (730)

F4

Generate a reviewed STR profile computer file (740)

F5

Deliver to system the reviewed STR profile computer file (750)

*FIG. 7*

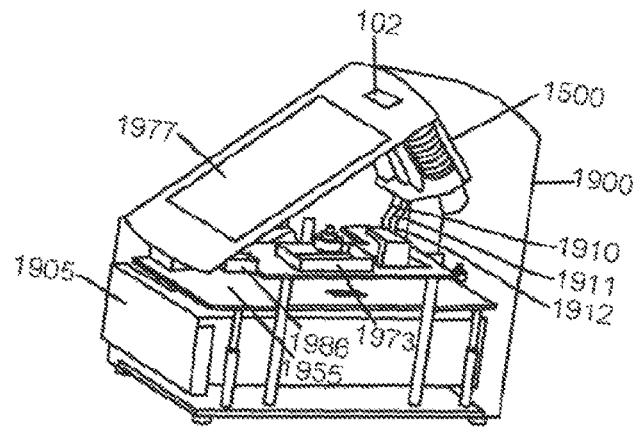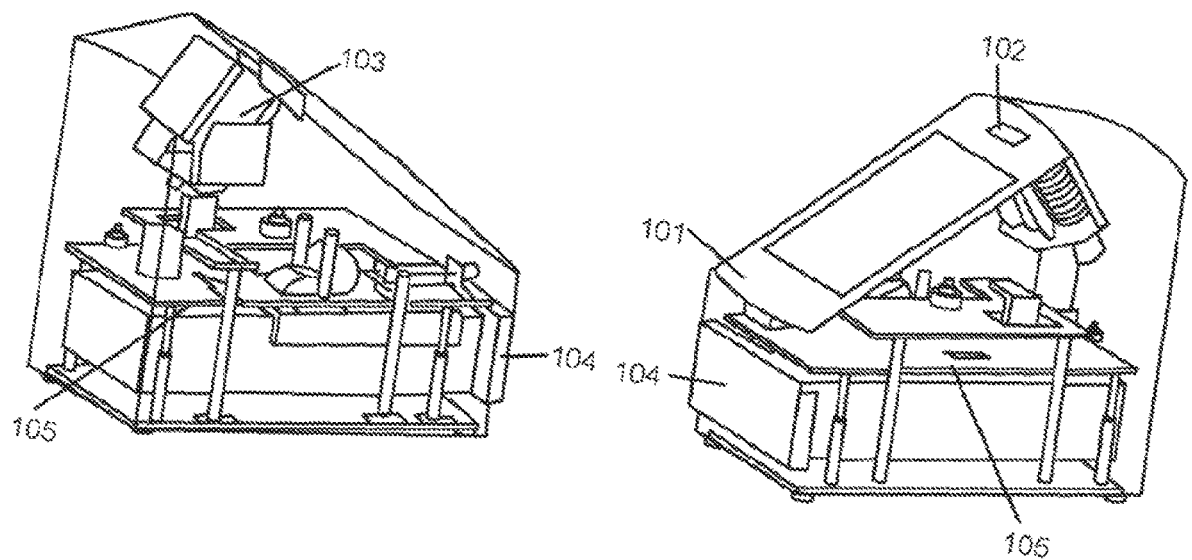
Fig. 9

CROWD-SOURCED AUTOMATED REVIEW OF FORENSIC FILES

CROSS-REFERENCE TO RELATED APPLICATIONS

This application is a divisional of U.S. application Ser. No. 15/570,730 filed Oct. 30, 2017, now U.S. Pat. No. 11,151,674, which is a nationalization of PCT Application No. PCT/US2016/30331, filed Apr. 30, 2016, which claims the benefit of and priority to U.S. Provisional Application No. 62/155,400 filed Apr. 30, 2015.

STATEMENT AS TO FEDERALLY SPONSORED RESEARCH

None.

COPYRIGHT NOTICE

Pursuant to 37 C.F.R. 1.71(e), applicant notes that a portion of this disclosure contains material that is subject to and for which is claimed copyright protection (such as, but not limited to, source code listings, screen shots, user interfaces, or user instructions, or any other aspects of this submission for which copyright protection is or may be available in any jurisdiction). The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

FIELD OF THE INVENTION

1. The Field of the Invention

The present invention relates to forensic analysis and logic systems. More particularly, it relates to computer systems and associated systems and methods that facilitate the collection, processing, analysis and/or validation of forensic data. In further embodiments, methods and/or systems for performing one or more transactions over a communication network are provided.

BACKGROUND

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

Short tandem repeat analysis (STR) is a molecular biology method used to compare specific loci on DNA from two or more samples. STR profiling is a method of biological forensic analysis that has become a worldwide standard for human identification in the forensic area. The particular STR alleles used by law enforcement agencies in various countries may differ. For example, CODIS (Combined DNA Index System), a program administered by the FBI, uses 13 STR loci, plus Amelogenin (AMEL) to determine sex. A standard European set uses 12 STR loci. Various law-enforcement agencies keep databases of STR profiles. These include databases in which the STR profile is associated with a known individual and databases in which the STR profile is not associated with an individual but may be associated with a crime scene. One such example is the Convicted Offender and Arrestee Index maintained by the FBI. The databases can be searched to determine whether an STR profile collected at a crime scene or from a suspect matches a profile in the database. An exact match is strong evidence of identity. Partial matches can be used, for example, as evidence of identity or of kinship.

STR profiles can be produced by integrated systems adapted to the task. These integrated systems generally include one or more computer systems or components to execute automated tasks such as performing the biological analysis, providing instructions and receiving input from operators of the system, and communication with other local or remote information handling systems. "Rapid DNA" or "Rapid Human ID" refers to the automated process of developing an STR profile from a reference sample, e.g., a buccal swab. Systems for performing Rapid Human ID include the RapidHIT® system available from IntegenX Inc. (Pleasanton, CA). See, for example, U.S. Pat. No. 8,894,946.

In one method, generating an STR profile involves the following steps: A biological sample, e.g., a forensic sample, is obtained for analysis. DNA from the sample is extracted and purified. Selected STR alleles are amplified, for example, by PCR. STR amplicons are detected, for example, by capillary electrophoresis and optical data collection. The collected data is processed for example by an integrated system to generate a computer file, typically including an STR profile.

Various software packages are available to process such data, including GeneMarker™ HID from SoftGenetics and GlobalFiler™ from Life Technologies. These packages produce an STR profile that can include an electropherogram in which peaks indicate STR amplicons. Such peaks can be annotated by the software package to "call" the allele identity. In some cases the software cannot call a peak with the requisite confidence. Such a peak may be flagged by the software. In certain jurisdictions, if the software package has been approved as "expert software," a computer file bearing no flags or meeting other quality criteria can be uploaded directly by the software package to a DNA database for searching. In some advanced integrated systems, many steps of the analysis, from chemically analyzing the sample to uploading a file to a DNA database for searching, to receiving the results of the searching are performed automatically under computer control to provide fast and efficient analysis and results with little or no ongoing human interaction required.

While this process works effectively for STR files that after processing are ready for upload to a forensic database or forensic service for searching, files having flags or otherwise not meeting quality criteria may need to be reviewed and revised or corrected by a forensic scientist before uploading. Automated STR systems at present generally indicate to an operator of the system one or more files that require review and then wait for a human operator to take action to have the file reviewed by a qualified expert such as a forensic scientist or to otherwise have the file checked or rerun to meet quality standards. The reviewed or corrected file may then be uploaded to a DNA database to determine a match. Review and correction of a file by a forensic scientist can improve the accuracy of allele calls in an STR profile, thereby improving the probability that a correct match will be found.

In the United States, a person cannot be held in custody for an unreasonable amount of time without being charged with a crime. Rapid Human ID systems as described above provide one rapid method that at various locations can collect and process DNA samples and upload the resulting STR forensic data for searching of a forensic database. If a match is found between the STR profile and an STR profile from a forensic sample in the database, there may be reason to link the person with crime associated with the profile in the database. However, when an STR file is flagged by the system, necessary review by a forensic scientist may not be immediately on site or available. Thus, STR files requiring review can cause substantial delays in completing the forensic analysis. Any delay between the time a file is generated by a system and the time that file is reviewed by a forensic scientist delays the time the file can be uploaded to a DNA database and a match determined. Such delay can result in release of a person in custody for whom a match may be found in the database.

A similar situation can arise with other types of forensic data tasks that require very quick performance or review by an expert. In some situations, two different DNA samples are processed (for example one from a crime scene and one from a person of interest) and the expert review needed is to determine if the profiles are a match. Again, time can be of the essence in particular situations and situations may arise at a time or place when experts are not generally available.

Other forensic situations requiring expert review might include matching or analyzing crime scene data such as fingerprints, shoe prints, tire prints, various objects or materials, etc.

SUMMARY

This disclosure provides, among other things, an improved automated STR system and method that combines automatic processing and decision making regarding STR profile files or other biological analysis or forensic files with the ability to take one or more further actions when flags are present in an STR file or an STR file does not meet one or more other quality standards to allow for automated uploading. An automated system identifies files that require further action (such as STR files with flagged peaks for allele calls) and initiates a repeat of the analysis that produced the file and/or generates one or more communications for forensic scientist review and communicates with forensic scientists service providers over a communication network for review of the files.

According to specific embodiments, an automated STR system determines a service provider, optionally based on specified criteria, and communicates with the service provider to facilitate review and/or revision of the STR file. The service provider reviews the file and provides a response that optionally includes or indicates a revised file for upload for further forensic matching. According to specific embodiments, an automated STR system can communicate with a number of service providers with respect to a particular file and authorize or select a service provider that can respond in the quickest time or according to other criteria.

In further embodiments, this disclosure provides a crowd-sourcing server system and method to match users or customers (such as various automated STR systems or operators of such systems or other users) that require a forensic report or biological analysis computer file, such as an STR profile computer file, to be reviewed by a forensic science service provider (e.g., a forensic scientist or scientific service provider) willing and able to perform the task.

Upon a request by a customer, service providers are alerted to the existence of a job. Services providers can bid to perform the job. The system chooses a service provided, optionally based on specified criteria, and provides access to the file to the service provider. The service provider reviews the file and provides a reviewed or revised file for upload to an external database for matching to the system. Advantages of systems and methods disclosed herein include decreased time between determination that a file requires review and review of the file and access to a corrected file for upload.

In other embodiments, other forensic analysis, such as DNA profile matching, can be forwarded to multiple forensic analysis service providers through a local or server crowd sourcing method as described herein.

Thus, according to specific embodiments, methods and/or systems and/or devices are described that can be used together or independently to provide improved automation in the collection, processing, analysis, and/or validation of forensic data. In specific embodiments, methods and/or systems and/or devices facilitate and/or automatically process data and send it to an external authority for matching purposes. In specific embodiments, methods and/or systems and/or devices facilitate and/or automatically flag data that does not meet quality standards or other criteria to be sent to an external authority and automatically take one or more actions to correct the data to meet the quality standards. According to specific embodiments, one or more automatic actions may include automatically causing data to be recaptured or automatically communicating with one or more external experts for review and revisions to the file.

Various embodiments of the present invention provide methods and/or systems for biometric data interaction over a communications network. According to specific embodiments of the invention, a client system is provided with a set of interfaces that allow a user to view, collect, validate, etc. biometric data. The client system can present information regarding the data and presents indications or instructions regarding actions a user should or can perform to complete the next step of the workflow. In response to a user action and completion of appropriate workflow steps, the client system sends to a server system the necessary information to access or process or verify biometric data. The server system uses the request data, and optionally one or more sets of server data, to process the request. According to specific embodiments of the present invention, a client system is, or has previously been, provided with an executable code file that allows the client system to operate as described herein.

An important application for the present invention, and an independent embodiment, is in the field of exchanging biometric data over the Internet or private networks, optionally using Internet media protocols and formats, such as HTTP, RTTP, XML, HTML, dHTML, VRML, as well as image, audio, or video formats etc. However, using the teachings provided herein, it will be understood by those of skill in the art that the methods and apparatus of the present invention could be advantageously used in other related situations where users access content over a communication channel, such as modem access systems, institution network systems, wireless systems, etc.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features according to specific embodiments are set forth with particularity in the appended claims. A better understanding of the features and advantages will be obtained by reference to the following detailed description that sets forth illustrative embodiments and the accompanying drawings (also "figure" and "FIG." herein), of which:

FIG. 6 shows an exemplary protocol for compensating a service provider.

FIG. 7 shows an exemplary protocol for bidding on a job by a service provider.

FIG. 9 shows several views of an example integrated forensic analysis system according to specific embodiments.

DESCRIPTION OF SPECIFIC EMBODIMENTS

Figure 1:
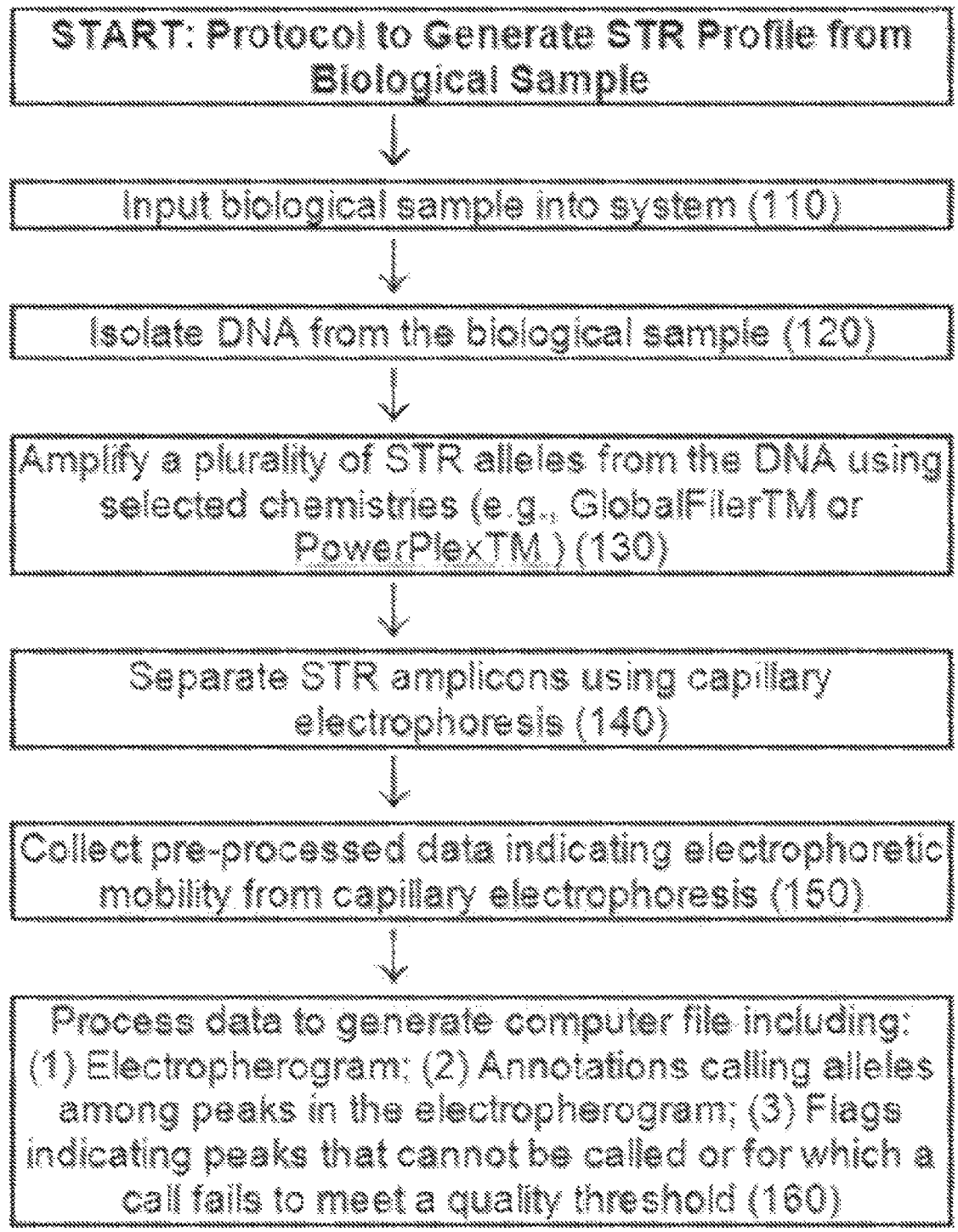
FIG. 1 shows an exemplary protocol to generate STR profile from biological sample.

Before describing the present invention in detail, it is to be understood that this invention is not limited to particular compositions or systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content and context clearly dictates otherwise. Thus, for example, reference to "a device" includes a combination of two or more such devices, and the like. Unless defined otherwise, technical and scientific terms used herein have meanings as commonly understood by one of ordinary skill in the art to which the invention pertains. Although any methods and materials similar or equivalent to those described herein can be used in practice or for testing of the present invention, the preferred materials and methods are described herein. While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed. Whenever the term "at least" or "greater than" precedes the first numerical value in a series of two or more numerical values, the term "at least" or "greater than" applies to each one of the numerical values in that series of numerical values. Whenever the term "no more than" or "less than" precedes the first numerical value in a series of two or more numerical values, the term "no more than" or "less than" applies to each one of the numerical values in that series of numerical values.

The term "sample", as used herein, refers to a sample containing biological material. A sample may be, e.g., a fluid sample (e.g., a blood sample) or a tissue sample (e.g., a cheek swab). A sample may be a portion of a larger sample. A sample can be a biological sample having a nucleic acid, such as deoxyribonucleic acid (DNA) or ribonucleic acid (RNA), or a protein. A sample can be a forensic sample or an environmental sample. A sample can be pre-processed before it is introduced to the system; the preprocessing can include extraction from a material that would not fit into the system, quantification of the amount of cells, DNA or other biopolymers or molecules, concentration of a sample, separation of cell types such as sperm from epithelial cells, concentration of DNA using an Aurora system (Boreal Genomics) or bead processing or other concentration methods or other manipulations of the sample. A sample can be carried in a carrier, such as a swab, a wipe, a sponge, a scraper, a piece punched out a material, a material on which a target analyte is splattered, a food sample, a liquid in which an analyte is dissolved, such as water, soda. A sample can be a direct biological sample such as a liquid such as blood, semen, saliva; or a solid such a solid tissue sample, flesh or bone.

Systems discussed herein can also be applied to process and analyze a sample that has been previously preprocessed, for example, by extraction of DNA from large object such as a bed sheet or chair and other processing which may include quantification of DNA concentration, cell concentration, or other manipulations before input of the pre-processed sample into the sample cartridge of the system. DNA can be analyzed by amplification (e.g., PCR) followed by capillary electrophoresis or by DNA sequencing, e.g., high throughput sequencing.

"Biometric data" as used herein generally refers to any data used to identify an individual, group of individuals, or any biologic entity or group that is a measurement or image of a biologic system. For purposes of this discussion, biometric data comprises without limitation, fingerprints, hand and foot prints, facial or body recognition, DNA or protein recognition, blood or tissue recognition, voice prints or vocal recognition, dynamic or static signature information, gait recognition, height, weight, dental records or xrays, etc. "Biometric data" can also encompass other identifying information, such as date of birth, government issued ID number, etc.

"Digitally captured biometric data" as used herein generally refers to any data used to identify an individual, group of individuals, or any biologic entity or group that is a measurement or image of a biologic system that is generally directly captured from a subject as digital data without requiring substantially further analysis or processing. For purposes of this discussion, biometric data comprises without limitation, fingerprints, hand and foot prints, facial or body recognition, voice prints or vocal recognition, dynamic or static signature information, gait recognition, height, weight, dental records or xrays, etc. "Biometric data" in some contexts can also encompass other identifying information, such as date of birth, government issued ID number, etc.

"Biochemical biometric data" as used herein generally refers to any data used to identify an individual or any biologic entity or group that is that is based on detecting one or more chemical or biological properties. For purposes of this discussion, "biochemical biometric data" biometric data comprises without limitation, DNA or protein recognition, blood or tissue recognition, or other chemical or biological substance analysis.

"Automated system" as used herein generally refers to a system that can request expert review of an STR file over a network. An automated system can be associated with a system for Rapid Human ID or with a more traditional forensic laboratory that generates STR profiles without use of a Rapid Human ID system. An "Automated system" as described herein can execute on the logic circuits of an integrated device such as a Rapid Human ID or can execute on the logic circuits of an associated computing device.

"User" as used herein generally refers to an entity that uses an automated system. Users are typically law enforcement agencies, but can be private.

"Crowd source server" as used herein generally refers to a system that matches customers, such as those using an automated system, with service providers.

"Customers" as used herein generally refers to users that use the crowd source server, either an entity operating an automated system, or other.

"Service provider" as used herein generally refers to an entity or individual that provides expert forensic review or matching of forensic data such as STR files.

"Expert review" as used herein generally refers to review or analysis of a forensic file or forensic data by someone qualified to perform the review.

"Expert reviewer" as used herein generally refers to a person performing expert review, typically as person accredited by an appropriate agency.

Overview

I. Automated Handling of an STR Profile Computer File by an Integrated System

US Patent application 20130115607 (Priority date Oct. 21, 2011, also published as WO2013059750A1) describes an integrated and automated sample-to-answer system that, starting from a sample comprising biological material, generates a genetic profile in less than two hours, for example where the biological material is DNA and the genetic profile involves determining alleles at one or a plurality of loci (e.g., genetic loci) of a subject, for example, an STR (short tandem repeat) profile, for example as used in the CODIS system. The system can perform several operations, including (a) extraction and isolation of nucleic acid; (b) amplification of nucleotide sequences at selected loci (e.g., genetic loci); and (c) detection and analysis of amplification product. These operations can be carried out in a system that comprises several integrated modules, including an analyte preparation module, a detection and analysis module, and a control module. Specific examples of other automated systems are discussed below and illustrated in FIG. 9.

Generation of a forensic computer file, such as an STR profile, can occur in a variety of settings. These include, for example, a mobile unit responding to a crime scene, a police booking station or a forensic laboratory. The sample being tested can include a sample taken from a crime scene or a sample taken from an individual directly.

Referring to FIG. 1, a system can generate an STR profile from a biological sample in the following way. A biological sample is input into system (110). DNA is isolated from the biological sample (120), e.g., by lysing cells, capturing DNA on a solid support and washing the DNA of waste. A plurality of STR alleles from the DNA is amplified using selected chemistries (e.g., GlobalFiler™ or PowerPlex™) (130). STR amplicons are separated by capillary electrophoresis (140). Pre-processed data is collected from the separation step, indicating electrophoretic mobility of the amplicons (150). Expert software is used to process data to generate a computer file (160). The computer file can include: An electropherogram; annotations calling alleles among peaks in the electropherogram; and flags indicating peaks that cannot be called or for which a call fails to meet a quality threshold.

Figure 2A:
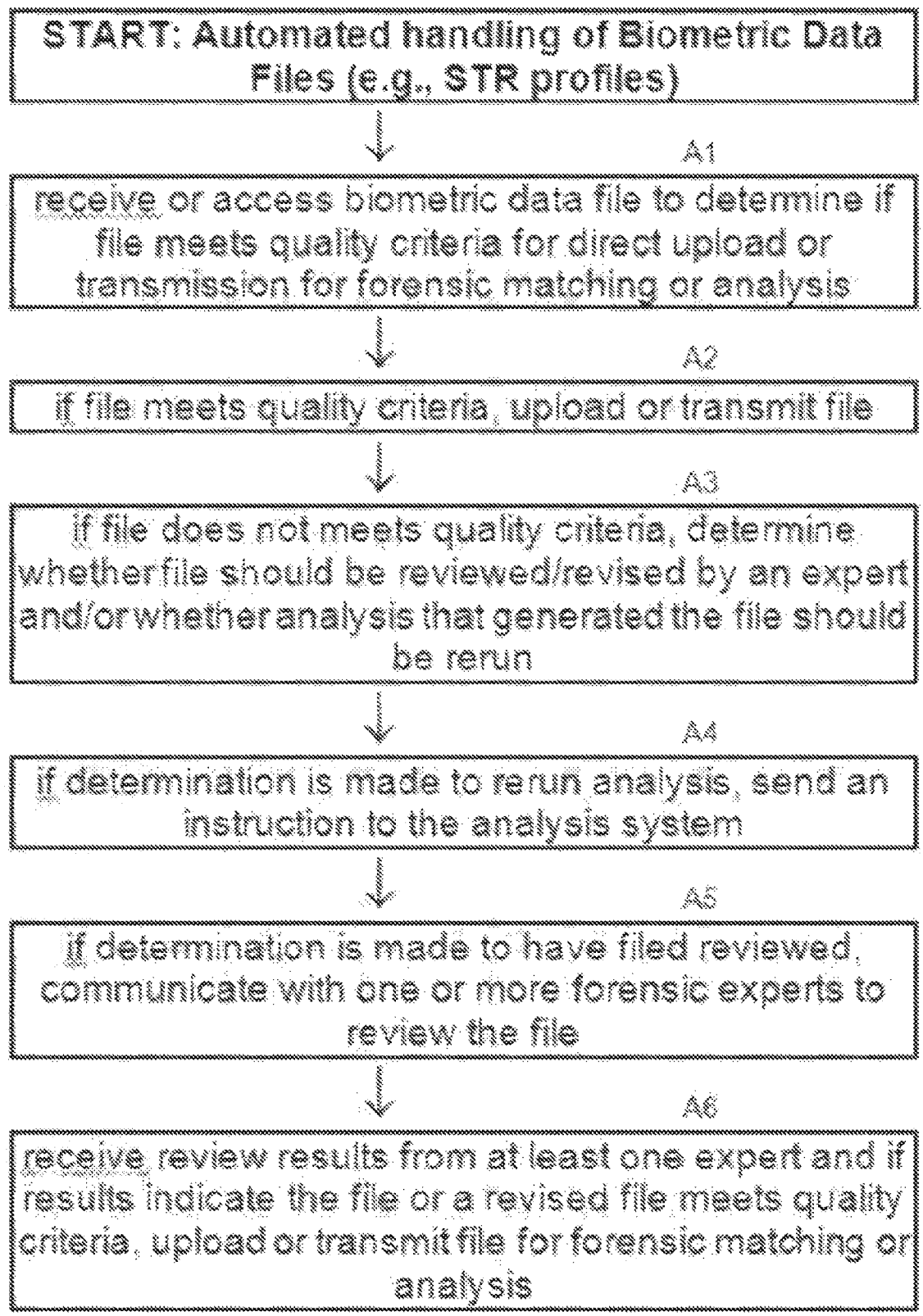
FIG. 2A-B illustrate two exemplary decision trees for deciding action on a computer file containing an STR profile.

FIG. 2A illustrates a general method for handling of a biometric data file by an automated system. These steps can be performed by executable logic incorporated into a system that also performs one or more steps to collect the biometric data or can be performed by a separate logic system that receives biometric data files from an analysis system.

The example method generally begins when a results biometric data file is available. (Step A1) The automated system reads the data file to determine if the file meets quality criteria for submission to the next forensic system, such as a DNA matching system and if the file meets the criteria, the automated system takes steps to initiate the process (Step A2). In the case of DNA matching, these steps can include uploading, emailing, or otherwise transmitting the file to whatever system will provide the final forensic report.

If the file does not meet quality standards, the automated system takes further steps to facilitate rapid forensic processing of the file. Quality standards can be variously configured by an operator or administrator of the automated system and can include various quality scores and/or specific data characteristics such as a number of times an allele call in an STR profile file is flagged. Further handling of the file can also be variously configured by an operator or administrator of the automated system and can include various criteria for taking one or more further handling actions. Thus, based on the criteria, the automated system makes a decision regarding the file (Step A3).

One determination that the automated system according to specific embodiments may make is to rerun the file. (Step A4). Various criteria configured at the system will aid in determining whether it is desirable to rerun the file and can include criteria such as: (1) the particular quality characteristics of the file, (e.g., some files may have so many flags that it is not desirable to have that file reviewed by an outside expert, or other quality characteristics may indicate that the analysis was sub-optimal); (2) the availability of the processing system to reprocess the sample and the expected speed of receiving reprocessing results; (3) the availability of service providers and the expected speed of receiving a corrected file; and (4) other criteria.

Another determination that the automated system according to specific embodiments may make is to request expert review of the file by communicating with one or more service providers. (Step A5). Various criteria configured at the system will aid in determining whether it is desirable to request an external review and how to request the external review can include criteria such as: (1) identities and contact information of one or more service providers stored at the system; (2) performance statistics or scores of one or more service providers stored at the system; (3) other criteria, such as cost, of one or more service providers stored at the system.

Once the decision is made to request expert review of the file, the automated system communicates to one or more experts to have the file reviewed. As discussed elsewhere herein, in specific embodiments, this communication can be multi-step and send out multiple requests that service provides respond to for review of the file, where the response can include cost and respond time proposals. The automated system can receive the responses and select a reviewer.

After expert review is completed, if the resulting file meets criteria, it is uploaded. (Step A6). As discussed further below, a file may be confirmed by an outside expert or the file or part of the file may be corrected by the expert.

An automated system may have two STR profile files that require matching, that is, a determination that the profiles are consistent with having been generated from genetic material from the same person. In some jurisdictions, profiles constitute a match when at least 8 STR alleles are the same. This process is referred to herein as "profile matching". In one embodiment of the disclosure, the automated system communicates with one or more experts for profile matching of the data files. Profiles delivered to the service provider can include electropherograms that do or do not include flags, and can include files in which none, one or both files has previously been reviewed by an expert reviewer. Accordingly, in addition to determining whether the profiles constitute a match, the expert reviewer also can review the files to analyze or re-analyze flagged items, and produce a reviewed or revised file. The service provider delivers to the user a report determining a match or mismatch between the files and, optionally, reviewed and/or revised profiles.

As will be understood in the art of logic systems, various specific actions can be used to implement the general functions described herein. For example, "sending a file" as discussed herein may involve actual transmission of a file via email or download or alternatively can involve sending a link or notification allow an expert to view a file on a local device that remains stored at the original site. Likewise, sending a confirmed or correct file may comprise transmitting a file or may comprise transmitting data indicating that a file is confirmed or transmitting data indicating corrections needed to a file. Furthermore, uploading a corrected file may be completed by the automated system after receiving the file or correction or confirmation data or in some implementations, the automated system can provide an active link or other directions that would allow a service provider to upload the file. Furthermore, a "file" includes one or more files.

Furthermore, an automated system implementing (Step A5) and (Step A6) above can perform numerous steps, as described in more detail below, to crowd source one or more forensic review requests to one or more forensic service providers.

Furthermore, while an automated system may be designed to perform one or more steps without local human interaction, this does not preclude systems that include a user interface allowing a user to confirm, modify, or cancel automated steps or otherwise to monitor or affect the automated process.

Figure 2B:
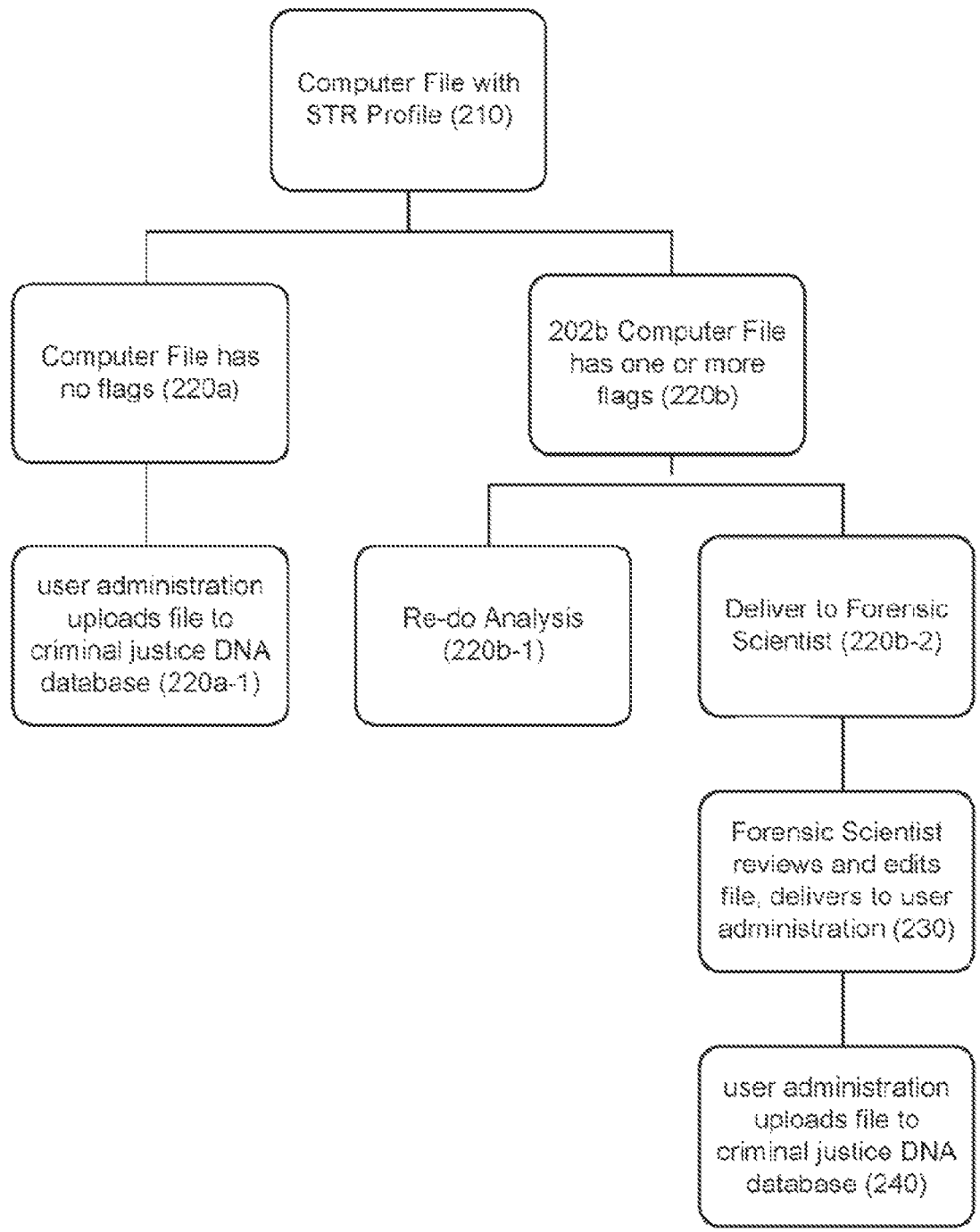

Referring to FIG. 2B, in a more specific example, once a system has generated an STR profile file (210), one or more further actions are taken with the file. As described herein, these further actions can be entirely automated, using one or more software components to decide on an action, or alternatively, one or more actions can include options for human intervention or human confirmation. In either case, further actions may be based on whether the file contains no flags (220a) or has one or more flags (220b). If the file has no flags, the system can upload the file to DNA database for searching (220a-1). If the file contains one or more flags, the system can decide between two options. One option (220b-1), involves requesting the analysis to be performed again. This can involve, for example, the system taking another sample from a subject and analyzing it with the system, or sending a sample to another facility for analysis. Another option (220b-2), involves delivering the file to a service provider for review. After the service provider has completed review and revision to the STR file, the revised file may be uploaded to a DNA database for matching (240). This upload may be done by the service provider or the revised file may first be delivered to the automated system (230), and the automated system may then upload the file to a DNA database for matching (240).

Figure 3:
FIG. 3 shows an exemplary protocol for dealing with an STR profile file containing flagged items.

Referring to FIG. 3, a protocol for having an STR profile file or other forensic data file reviewed can include the following steps: The system delivers computer file bearing flagged item to service provider (310). A service provider in receipt of a computer file containing flags performs a review. Objects of the review include clearing flagged items and/or confirming the file meets a quality control standard. According to specific embodiments, reviewing a computer file containing a flagged peak, the service provider may do any of the following: (i) Confirm the call of the flagged peak made by the software; (ii) Change or assign a call to a flagged peek, (iii) Delete a call made by the software or (iv) Do nothing (320). Service provider delivers reviewed file to automated system (330) and the automated system uploads reviewed file to a criminal justice DNA database (340).

II. Automated Handling of Service Provider File Review

Thus, as described above, a review of a forensic file may be handled by an integrated automated system that performs some or all of the functions of communicating with various service providers, receiving bids or job acceptance requests, and assigns jobs to service provides and receives results. Alternatively or additionally, a review request may be communicated to a crowd-source server as described below that handles some or all communications with service providers.

In either alternative, service providers typically will contract with the system operator to provide the service "on-demand" for certain compensation. Other arrangements to form a contract to perform services may be used, such as one-sided contracting, in which the job is broadcast for performance by anyone. Individuals who contract with the service operator are referred to herein as "service providers". Service providers can be pre-qualified to perform the file review. For example, a service provider may be required to have the requisite skills to perform a review of a forensic file or to have passed a licensing examination. Such a person may already possess such skills, or may be trained, e.g., by the person or entity, to gain such skills.

Service providers can be assigned a quality rank based on desired factors such as accuracy of review, speed of review or physical location. In certain jurisdictions, an STR profile computer file, if it is to be reviewed, must be reviewed by a person physically located in a certain jurisdiction, such as a U.S. state.

Service providers can be compensated for performing a job in any number of ways. These include, for example, a fixed fee per file reviewed, a sliding fee based on difficulty of the file, e.g., number of flags in a file, or speed of turn-around. Such terms may be agreed upon in advance of accepting a particular job. Compensation may be made after each instance of performing a job, or at periodic time periods, such as semi-monthly. Compensation can be arranged electronically, for example by direct deposit to a bank account, or by physical check.

Methods performed by a computing device are performed programmatically, that is, through the use of code or computer-executable instructions, e.g., software, executable by one or more processors. These instructions may be carried on a non-transient computer-readable medium.

The system can include processors and computer-readable media including which, when executed, carry out steps of the methods of this disclosure.

In operation, the method can involve some or all of the following steps: receiving notification from a user of a job to be performed, e.g., review of an STR profile computer file, notifying service providers of a job to be performed; receiving an indication from one or more service providers of their willingness to perform the job; selecting a service provider who has indicated their willingness to perform the review; providing access to the computer file to the selected service provider; having the service provider review the file; and receiving from the service provider a reviewed file.

The user can provide the computer file before or after a service provider has been selected to perform the job. The user also can specify qualities desired or necessary in the service provider, such as level of training, physical location, turn-around time, error rate, etc. The request can be made directly from an expert system that generates the profile and that accesses the communications network directly, or by a person who submits the job.

Service providers agree to receive notifications from the service operator that an STR profile file is available for review. Service providers have the option to respond to a notification indicating their willingness to review the file. If selected to review the file, the selected service provider may review the file and annotate it, for example by addressing flagged items, and provide the reviewed file to the organization.

A service provider can receive an alert through any appropriate computing device. For example, the device can be a smart phone, a tablet, a laptop computer, a desktop computer or a television. These may be provided with network connectivity through cell service, wireless Internet, etc. Processing resources can enable service providers communicate with users or customers over a suitable communications network.

Figure 4:
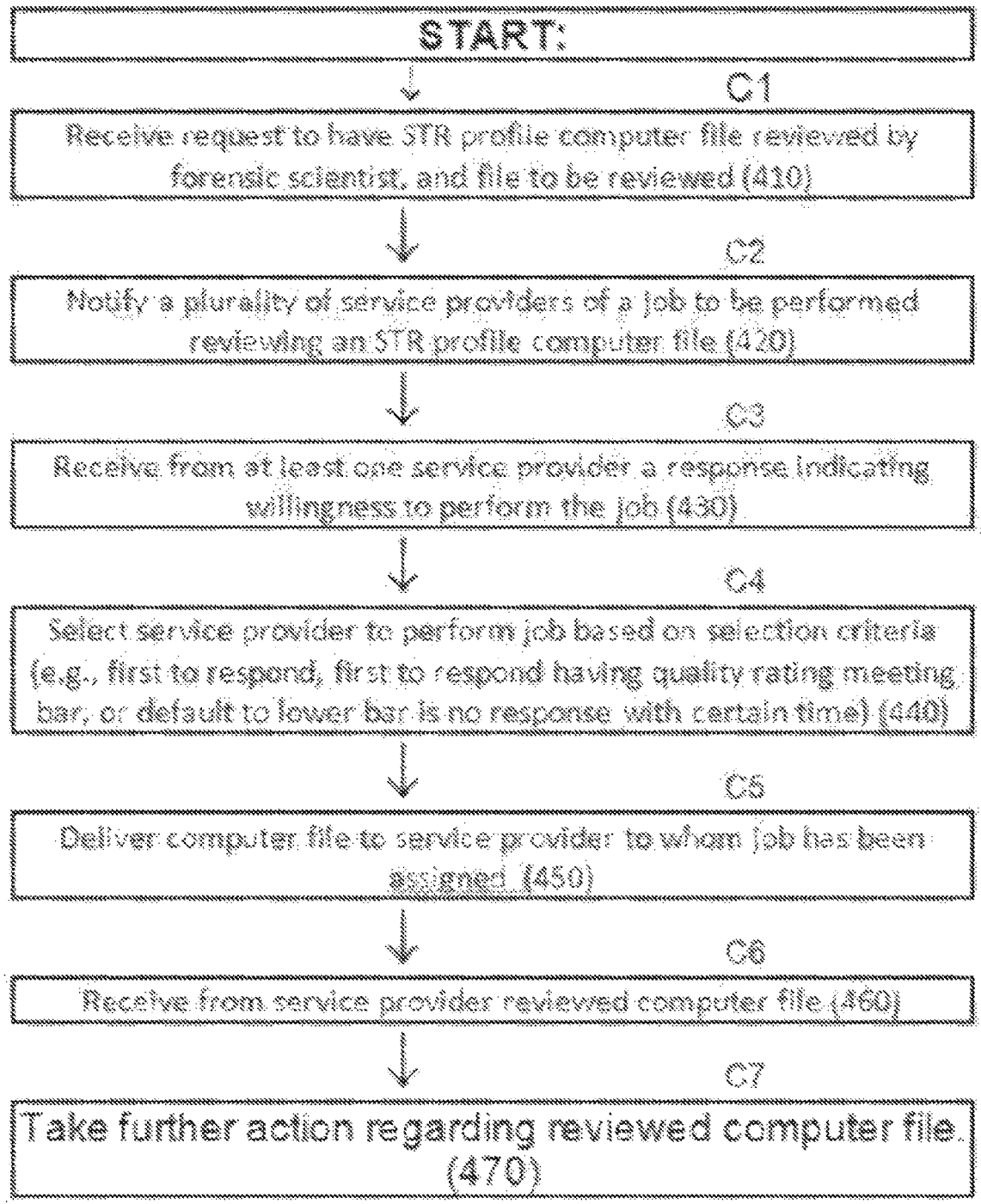
FIG. 4 shows an exemplary protocol for automatically crowd-sourcing the review of flagged STR profile file.

In one embodiment, crowd sourcing is used to select a service provider to review an STR profile file, either by an automated forensic system or via a crowd-sourcing server. Referring to FIG. 4, over a communications network, a request is received to have a job done, e.g., review of a forensic report computer file (410). A plurality of service providers are notified of job to be performed (420).

Any suitable communications network can be used, such as cell or Internet. The notification may be in the form of a phone call, a text message, a mobile device notification, etc. Notification can come through an application designed for a mobile device or a computer. The notification can include a "response time," a time within which a person selected to perform a job must complete the job. Such a time may be no more than any of 10 hours, 2 hours, 1 hour, 30 minutes, 10 minutes or 5 minutes.

Once notified, a service provider can indicate that they are willing to accept the job or reject the job (430). Or, they may simply ignore the notification. The indication can be made over a communications network that can be the same or different than the network that provided the notification. Individuals who indicate they are willing to accept the job are referred to as "bidders".

The system (whether an automated system or crowd sourcing server) can now select one or more bidders to perform the job of reviewing the STR profile file (440). Selection can be made based on any number of criteria. In one embodiment, the first service provider to bid for the job is selected. In another embodiment, the first service provider having a specified qualification ranking may be selected, e.g., a certain turn-around time or accuracy score. An individual selected to perform a job is referred to as a "selected service provider".

Once a bidder is selected as a selected service provider, the system delivers the computer file to be reviewed to the selected service provider (450). The computer file can be delivered in any number of ways. For example, an application can allow the selected service provider to click through to the file. The selected service provider may be able to enter a website location from which the file can be accessed. Alternatively, the file can be provided by email.

The selected service provider reviews the file, making any changes necessary. The reviewed file can be saved over the original file or as a new file.

The selected service provider then delivers the reviewed file to the system (460). Delivery can be by any suitable route, including the route by which the file was delivered to the selected service provider.

Figure 5:
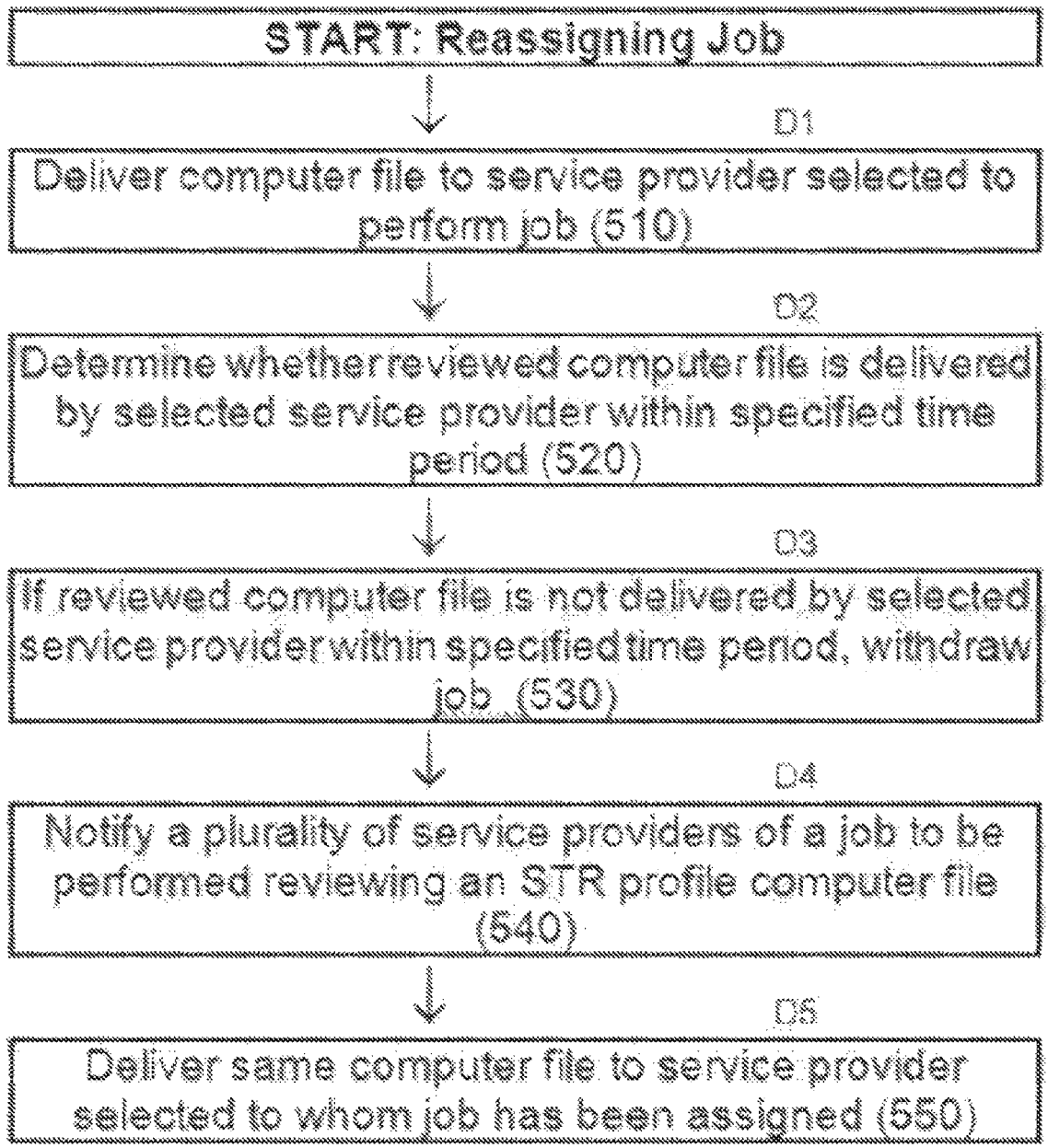
FIG. 5 shows an exemplary protocol for reassigning a job.

In certain embodiments, a job may be withdrawn from a selected service provider under various circumstances, such as failure to deliver a file within a certain amount of time. Referring to FIG. 5, a computer file to be reviewed is delivered to a selected service provider (510). The system determines whether the selected service provider has delivered the file within a specified time period (520). If not, the job is withdrawn, and access to the computer file terminated (530). At this point, the system can notify service providers of the job, which may or may not be identified as the same job previously posted (540). A service provider submitting a bid is selected, and the file is delivered to the selected service provider (550). Typically, the service provider who failed to deliver within the specified time is locked out of the bidding process for the repeat job. Once received, the system delivers the reviewed file to the user or customer (550).

After performing the job, the service provider can be compensated for their work, as set forth in FIG. 6. Activity from the perspective of a service provider is shown in FIG. 7.

Figure 8:
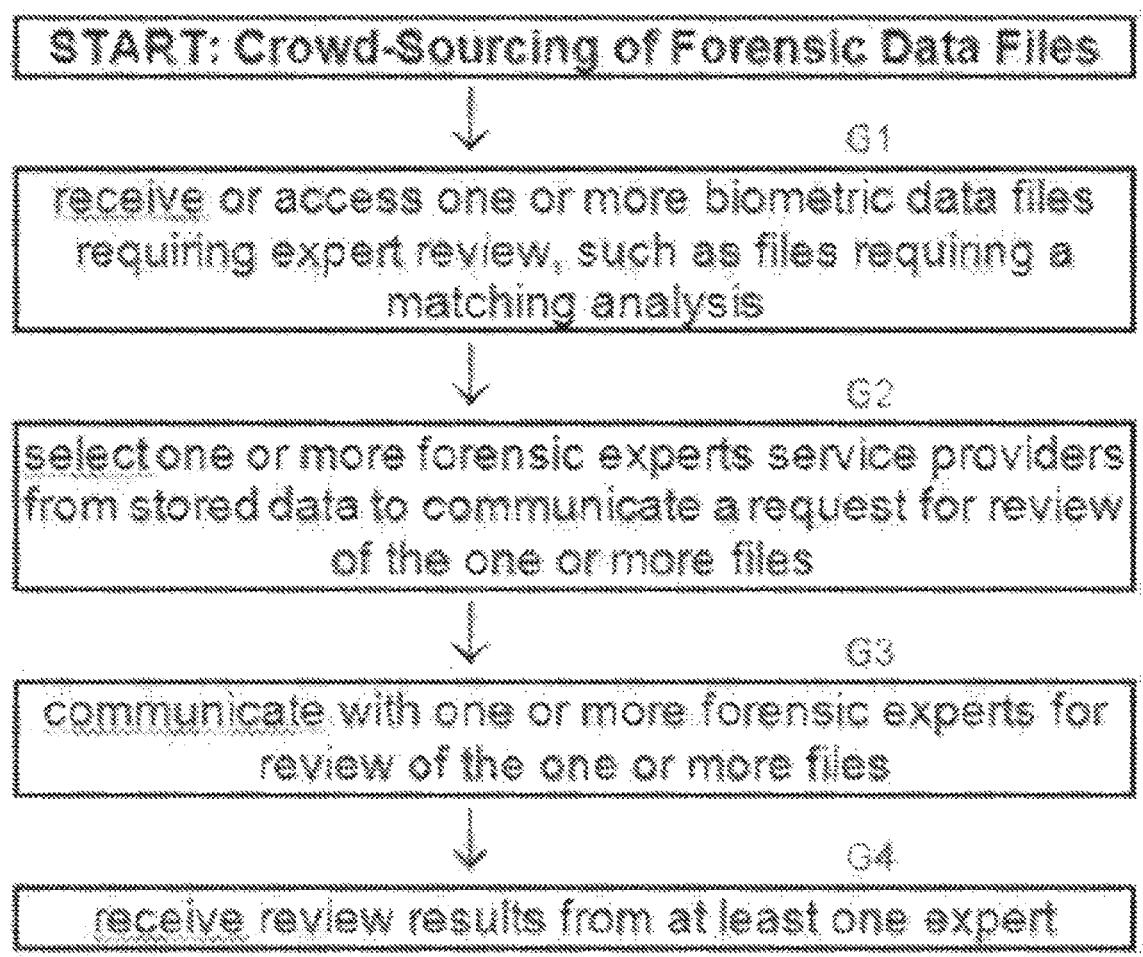
FIG. 8 shows an exemplary protocol for acquiring expert review of forensic data.

FIG. 8 shows an exemplary protocol for acquiring expert review of forensic data. This figure represents a protocol where the forensic data requiring analysis is any form of forensic data that can be represented in a digital file. Such data might include multiple STR files that require comparison one to another. Multiple fingerprints or other prints including partial prints that require comparison, etc. As above, these steps can be performed by executable logic incorporated into a system that also performs one or more steps to collect forensic data or can be performed by a separate logic system. Also, these steps can be performed by a local device or using a crowd sourcing server.

As will be understood in the art, whether or not a single "file" contains multiple sets of data (such as multiple STR profiles, multiple prints, etc.) or whether the sets of data are sent in multiple files in an implementation detail that can vary according to specific embodiments. Thus, as used herein throughout, file and files are generally equivalent terms except where the context requires otherwise.

The example method generally begins when one or more forensic data files are available for review. The system receives or accesses instructions for the type of review required (e.g., multiple-sample STR data sets for matching) and determines how to handle the file or files. File handling can be variously configured by an operator or administrator of an automated system or crowd sourcing server and can include various criteria for taking one or more further handling actions. The system makes a determination to request expert review of the file by communicating with one or more service providers. Various criteria configured at the system will aid in determining whether it is desirable to request an external review and how to request the external review can include criteria such as: (1) identities and contact information of one or more service providers stored at the system; (2) performance statistics or scores of one or more service providers stored at the system; (3) other criteria, such as cost, of one or more service providers stored at the system.

Once the decision is made to request expert review of the file or files, the automated system communicates to one or more experts to have the file reviewed. As discussed elsewhere herein, in specific embodiments, this communication can be multi-step and send out multiple requests that service provides respond to for review of the file, where the response can include cost and respond time proposals. The system can receive the responses and select a reviewer. As discussed above, files delivered to the service provider can include electropherograms that do or do not include flags, and can include files in which none, one or both files has previously been reviewed by an expert reviewer. Accordingly, in addition to determining whether the profiles constitute a match, the expert reviewer also can review the files to analyze or re-analyze flagged items, and produce a reviewed or revised file. The service provider delivers to the user a report determining a match or mismatch between the files and, optionally, reviewed and/or revised profiles.

III. Crowd-Sourced Server for STR or Forensic File Review

According to further specific embodiments, disclosed herein are systems and methods for creating a crowd-sourcing server for review of an STR profile computer file that can be accessed over a communication network by automated systems as discussed above or can be accessed by any other person or systems with forensic files needing review. According to specific embodiment, a crowd-sourcing server receives job requests from one or more customers with STR files requiring review. The crowd-sourcing server then communicates or provides or assigns requests to one or more service providers. In one embodiment, a system communicates with customers (e.g., automated STR systems, other STR analysis, or any person or organization desiring review of a forensic file or analysis file) and service providers to receive a request to perform a job reviewing a computer file, and to communicate availability. One service provider who indicates willingness to perform the job is provided access to the computer file. The selected provider performs the review. The reviewed computer file is provided to the customer and/or optionally directly uploaded to an external database.

The customer may be any person or organization or automated system having such a file. These include law enforcement agencies and may be forensic laboratories, booking stations or mobile labs. The STR profile computer file can be generated manually or by an automated and integrated instrument, for example, one configured to perform Rapid Human ID.

The system can include a user interface through which the user communicates with the server. This can include a graphical user interface for use by a human administrator. Alternatively, the interface can involve machine-to-machine code by which an expert system places a request with the service system operator.

According to specific embodiments, methods and systems as described herein are incorporated into systems for physical sample collection and analysis as discussed in above referenced applications. Example systems comprise a user GUI for interacting with the system and in specific embodiments a GUI indicates to a user that sample analysis is in progress once the user has completed all necessary sample preparation. According to specific embodiments, an "in progress" or similar status message presented at the system will continue during the time that an expert review is requested and is pending. According to specific embodiments, the same message can be displayed before expert review is requested and during expert review. In these example embodiments, expert review requested and received by the system can be made effectively invisible to the user so that the immediate user experience is the same whether the system determines expert review is desirable and requests such a review. In alternative example systems, a GUI can indicate that expert review has been requested and is on-going. Thus, according to specific embodiments, a system for analysis provides a seamless user experience whether or not expert review is employed.

Example Automated System

Recognized herein is the need for highly integrated and automated systems and methods for collecting digitally captured and biochemical biometric data, automated systems as described herein may be capable of preparing, processing and analyzing a single sample or a plurality of samples. Several automated sample handling operations can be performed by the system provided herein, for example, (a) receiving one or more samples; (b) isolating and extracting target material from the received sample; (c) purifying and amplifying the whole target material or selective portion of the target material to produce an analyte ready to be examined; and (d) separating, detecting and analyzing the prepared analyte. Systems provided herein can be fully automated, enabling a user to receive, process and analyze a sample without substantial labor and input. Sample preparation, processing and analysis can be accomplished in provided systems without the necessity of manually removing and transferring the sample, reagents and analytes among different parts in the system. Since the incorporated sub-units (e.g., sample cartridge and electrophoresis cartridge) are highly integrated and bear small sizes, systems provided herein can be dimensioned to minimize footprint, enabling the portability and usefulness in a wide context of applications. For example, the systems may be used in on-the-go situations, such as remote locations. Or they may be used in situations in which transportation is not readily available or user mobility is desired, such as battlefields scenarios.

FIG. 9 shows portions of one example automated system that can embody one or more aspects of specific embodiments. In this example, a cartridge interface 103 and an electrophoresis interface 105 engage a DNA sample cartridge and an electrophoresis reagent cartridge. Both the sample cartridge and the electrophoresis cartridge provided herein can be releasably or removably engaged with the system. The system of FIG. 9 can be used in forensic analysis to decode the genetic information of a single sample. In some cases, the system may be used to determine the genetic profile (e.g., the STR file) for a sample in less than about 6 hours, 5 hours, 4 hours, 3 hours, 2.5 hours, 2 hours, 1.5 hours, 1 hour, 30 minutes, 20 minutes, 10 minutes, 5 minutes 1 minute or less. Such time may depend upon the number of steps included in sample processing operations, for example.

Figure 10:
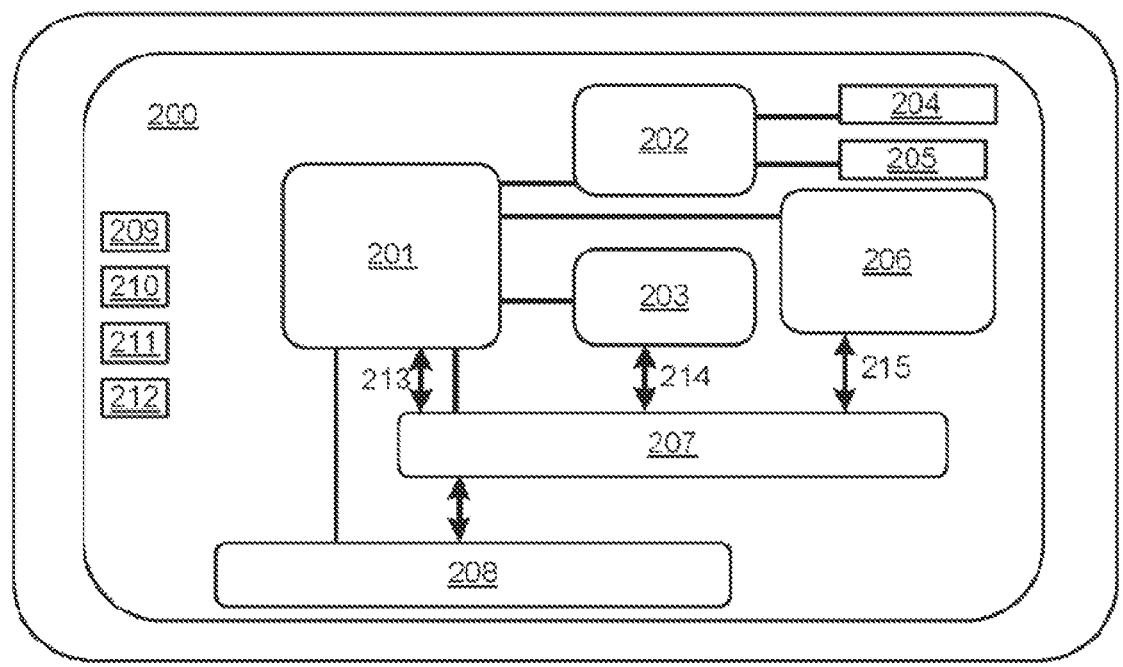
FIG. 10 is a functional block diagram of an example automated system according to specific embodiments.
Figure 11:
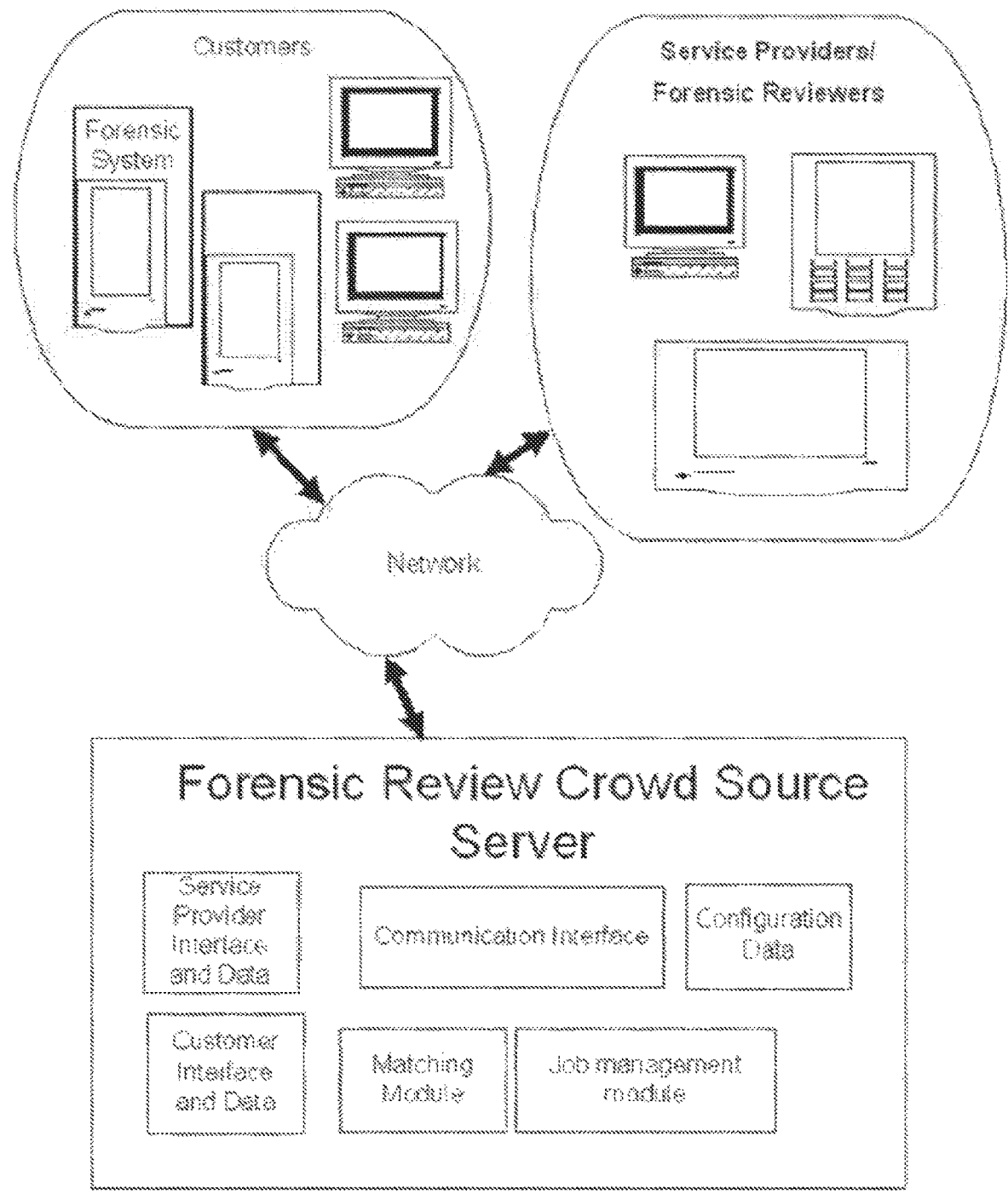
FIG. 11 is a block diagram showing a plurality of forensic systems with automated systems for contacting a service provider for an expert review according to specific embodiments.
Figure 12:
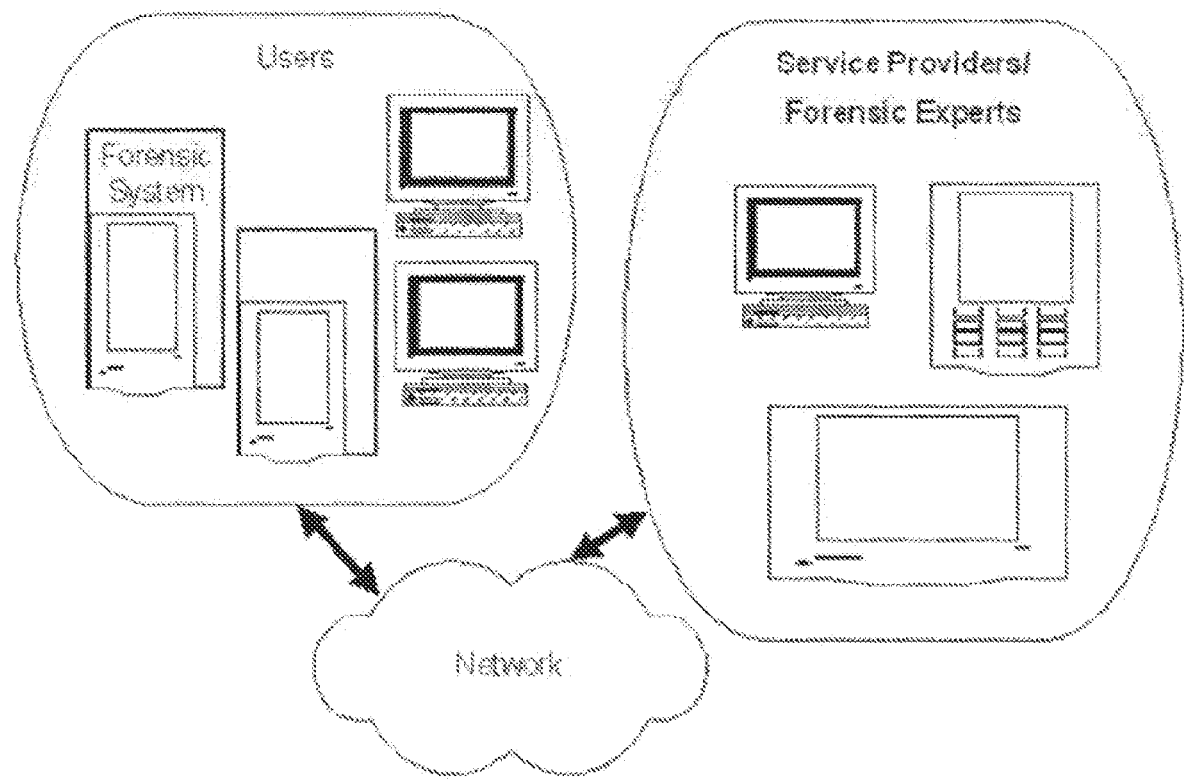
FIG. 12 is a block diagram of an example crowd-sourcing server automated system according to specific embodiments.

An example schematic of such an example system is illustrated in FIG. 10. A chassis 200 is shown and generally provides for structural support. This chassis may be formed of a metallic material, such as aluminum or steel, a polymeric material, or a combination thereof. In some cases, the chassis may be structured to minimize the weight of the system. A user interface which comprises system electronic controls 201, embedded computer 202, and a user interface screen capable optionally capable of identifying and reading fingerprint 204 and sample patch barcode 205, is shown. The user interface receives and processes requests or instructions from a user and delivers information to a local user at the system. An example system according to specific embodiments includes software or logic modules configured to execute routines for performing the operations described above and transmit and receive information, such as computer files, from remote locations, e.g., over the internet. The user interface can also enable the user to monitor the progress of the operation and make changes to the operation of system if measurements are not within selected parameters. A sample cartridge interface 206 is provided for receiving a sample cartridge for sample processing. Also comprised in the system is a fully integrated electrophoresis cartridge 207 that is releasably engageable with the system via an electrophoresis cartridge interface. The electrophoresis system comprises all essential parts for performing an electrophoretic analysis, such as an electrophoresis capillary, electrodes (e.g., anode and cathode), electrophoresis separation medium, or electrophoresis buffer. It may further comprise one or more reagent container for holding reagents that are used for sample processing, e.g., a lysis buffer container. The lysis buffer may be placed in fluidic communication with the sample cartridge and used for isolating the target material out of the sample during sample processing, after both the sample cartridge and the electrophoresis cartridge are engaged with the system. Once the engagement of the electrophoresis cartridge is completed, at least one automatic communication between the electrophoresis cartridge and the system may be established, for example, an electrical communication 213 between the electrophoresis cartridge and the system electronic controls 201, an optical communication 214 between a portion of the electrophoresis capillary in the electrophoresis cartridge and an optics module 203 of the system, a fluidic communication 215 between a sample inlet port of the electrophoresis cartridge and a sample outlet port of the sample cartridge, a mechanical and thermal 216 communication between the electrophoresis cartridge and a motorized drives and cooling module 208 of the system.

The system provided herein may further comprise a power source 212 for supplying the power for the system, AC mains 211 for applying a voltage gradient across the anode and the cathode, one or more fans 210 for dissipate the heat for one or more parts of the system, and one or more USB ports 209 for collecting and transferring data either within the system or outside the system.

Computer Control Systems

Figure 13:
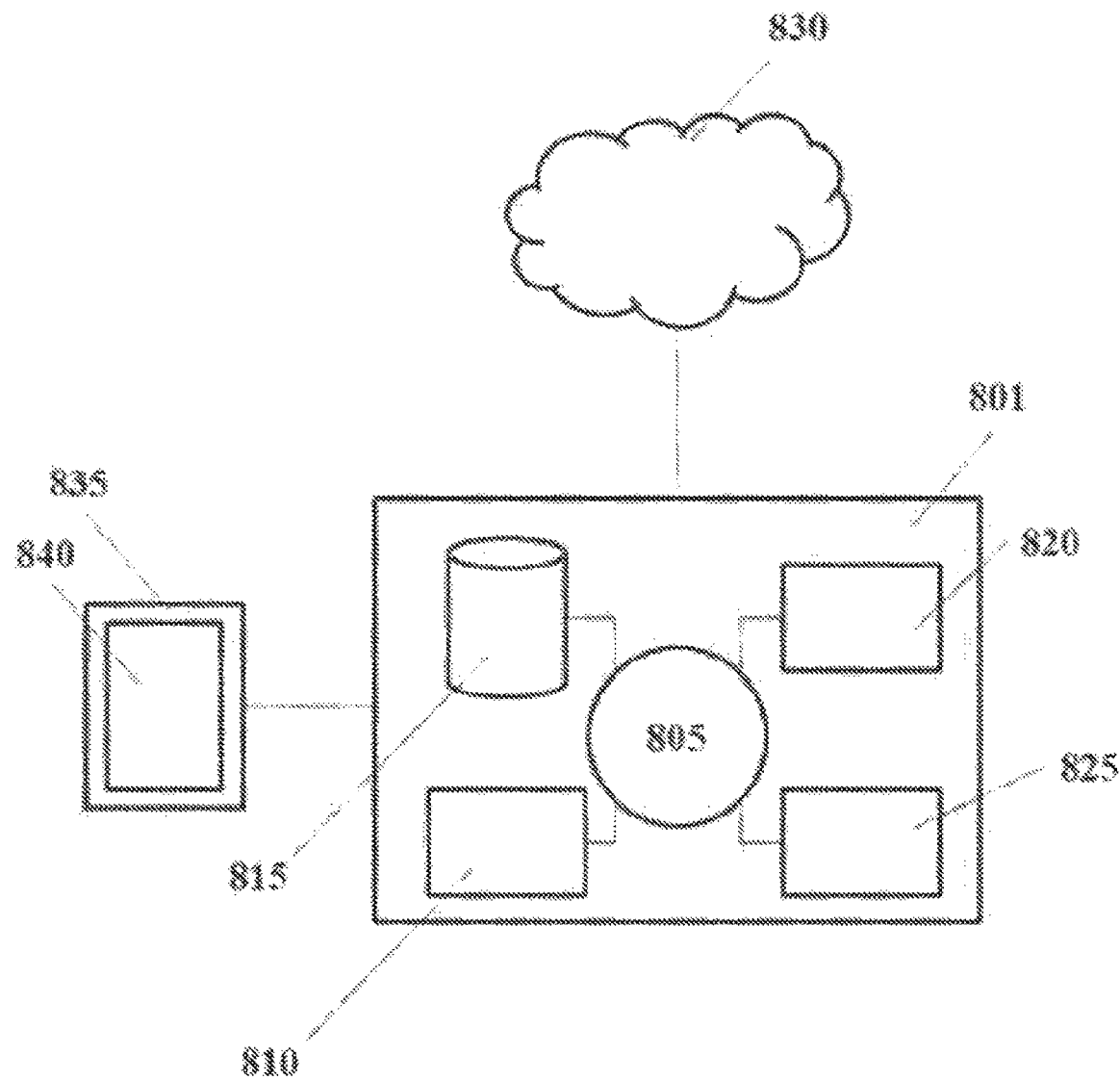
FIG. 13 shows a computer system that is programmed or otherwise configured to handle forensic data files as described according to specific embodiments herein.

FIG. 13 shows a computer system that is programmed or otherwise configured to handle forensic data files as described according to specific embodiments herein. All of part of such a system can be included in an automated integrated system such as shown in FIG. 9. FIG. 13 shows a computer system 801 that is programmed or otherwise configured to perform automatic results communication, file uploading, and communication for service provider review as described herein. The computer system 801 according to specific embodiments can regulate various aspects of sample preparation, processing and/or analysis of the present disclosure, such as, as well as providing for the confirmation of STR profiles or other forensic data using forensic experts or crowd sourcing as described herein. The computer system 801 can be in whole or in part integrated with an automated analysis system or may comprise one or more hardware components separate from an integrated analysis system but in communication with an analysis system.

The computer system 801 includes a central processing unit (CPU, also "processor" and "computer processor" herein) 805, which can be a single core or multicore processor, or a plurality of processors for parallel processing. An example computer system 801 generally includes memory or memory location 810 (e.g., random-access memory, read-only memory, flash memory), electronic storage unit 815 (e.g., hard disk, volatile or non-volatile memory, interface with cloud storage, etc.), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as interconnects on a motherboard on in an integrated circuit. The storage unit 815 can be a data storage unit (or data repository) for storing data. The computer system 801 can be operatively coupled to a computer network ("network") 830 with the aid of the communication interface 820. The network 830 can be the Internet, an Internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system, 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840, for example, for enabling the user to instruct the computer system 801 to begin sample preparation, processing and/or analysis and for providing user options regarding handling of STR files. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805. The algorithm can, for example, implement the general operation of a system for sample preparation, processing and/or analysis. In some examples, the algorithm can regulate the sequential opening and closing of valves or the operation of an electrophoresis cartridge.

According to specific embodiments, a computer system 801 can be configured as an automated STR system or component of an automated STR system that among other functions uses one or more user input mechanisms to receive configuration data regarding one or more service providers, such as service providers and to store that data for use when an STR file containing flags is encountered. As described herein, the system communicates with service provides using external communication interfaces, such as 830. Such communication as described herein can include requesting bids for jobs, assigning jobs, receiving results, and taking further action with results.

According to other embodiments, a computer system 801 can be configured as a crowd-sourcing server to communicate with multiple customers with STR or similar files requiring forensic review and multiple service providers providing such review as discussed herein.

Embodiment in a Programmed Information Appliance

Figure 14:
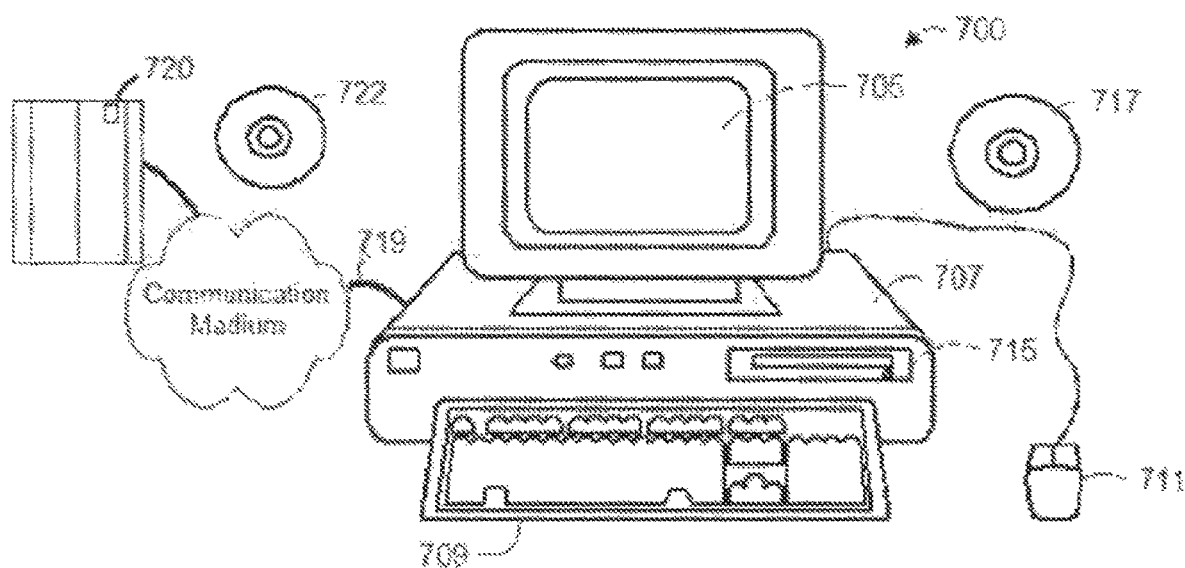
FIG. 14 is a diagram showing a representative example logic device in which various aspects of the present invention may be embodied.

FIG. 14 is a diagram showing a representative example logic device in which various aspects of the present invention may be embodied. As will be understood to practitioners in the art from the teachings provided herein, specific embodiments can be implemented in hardware and/or software. In some embodiments, different aspects can be implemented in either client-side logic or server-side logic. As will be understood in the art, specific embodiments may involve a non-transitory, tangible, fixed media program component containing logic instructions and/or data that when loaded into an appropriately configured information device cause that device to perform according to the invention. As will be understood in the art, a fixed media containing logic instructions may be delivered to a user on a fixed media for physically loading into a user's computer or a fixed media containing logic instructions may reside on a remote server (e.g., a cloud server) that a user accesses through a communication medium in order to download or execute a program component.

FIG. 14 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a desktop or workstation computer system as illustrated in 700, containing CPU 707, optional input devices 709 and 711, non-transitory storage (e.g., disk drives) 715 and optional output screen 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection. While the illustrated embodiment is a workstation, it will be understood in the art that a wide variety of information devices, including tablets, smart phones, diagnostic equipment, other networked equipment, etc., can also be involved in specific embodiments and will have components corresponding to the illustrated components.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

OTHER EMBODIMENTS

The invention has now been described with reference to specific embodiments. Other embodiments will be apparent to those of skill in the art. In particular, a user digital information appliance has generally been illustrated as a personal computer. However, the digital computing device is meant to be any information appliance for interacting with a remote data application, and could include such devices as a digitally enabled television, cell phone, personal digital assistant, laboratory or manufacturing equipment, etc. It is understood that the examples and embodiments described herein are for illustrative purposes and that various modifications or changes in light thereof will be suggested by the teachings herein to persons skilled in the art and are to be included within the spirit and purview of this application and scope of the claims.

Furthermore, various different actions can be used to effect biometric communication between a user and a biometric biochemical analysis system. For example, a voice command may be spoken by the user, a key or screen area may be indicated, a button or screen area on an associated module or component may be indicated, or selection using any pointing device may be effected by the user.

All publications, patents, and patent applications cited herein or filed with this application, including any references filed as part of an Information Disclosure Statement, are incorporated by reference in their entirety.

The general structure and techniques, and more specific embodiments that can be used to effect different ways of carrying out the more general goals are described herein. Although only a few embodiments have been disclosed in detail above, other embodiments are possible and the inventor (s) intend these to be encompassed within this specification. The specification describes specific examples to accomplish a more general goal that may be accomplished in another way. This disclosure is intended to be exemplary, and the claims are intended to cover any modification or alternative that might be predictable to a person having ordinary skill in the art. Also, the inventors intend that only those claims which use the words "means for" are intended to be interpreted under 35 USC 112, sixth paragraph. Moreover, no limitations from the specification are intended to be read into any claims, unless those limitations are expressly included in the claims. The logic components described herein may be any kind of components, either general purpose, or some specific purpose components. The component architecture may be an Intel or AMD based architecture or any other logic processing architecture. An operating system, such as Linux, Unix, Windows, etc. may be included to provide various information handling functions. One or more components may include a handheld computer, such as a PDA, cell phone, or laptop, a handheld camera, etc.

The programs may be written in C or Python, or Java, Brew or any other programming language. The programs may be resident on a storage medium, e.g., magnetic or optical, e.g., the computer hard drive, a removable disk or media such as a memory stick or SD media, wired or wireless network based or Bluetooth based Network Attached Storage (NAS), or other removable medium, or other removable medium. The programs may also be run over a network, for example, with a server or other machine sending signals to the local machine, which allows the local machine to carry out the operations described herein.

Where a specific numerical value is mentioned herein, it should be considered that the value may be increased or decreased by 20%, while still staying within the teachings of the present application, unless some different range is specifically mentioned. Where a specified logical sense is used, the opposite logical sense is also intended to be encompassed.

A system of this disclosure can communicate through a communications network with both those requesting the service of having a file reviewed, and service providers willing to provide these services. The communications network can be any electronic communications network. Network connectivity can be through any medium, such as cell service, Internet, radio, television, etc. The interface with the customer/user or service provider can be any appropriate computing device. For example, the device can be a smart phone, a tablet, a laptop computer, a desktop computer or a television.

While preferred claims of the present invention have been shown and described herein, it will be obvious to those skilled in the art that such claims are provided by way of example only. Numerous variations, changes, and substitutions will now occur to those skilled in the art without departing from the invention. It should be understood that various alternatives to the claims of the invention described herein may be employed in practicing the invention. It is intended that the following claims define the scope of the invention and that methods and structures within the scope of these claims and their equivalents be covered thereby.

Software Implementations Various embodiments involving methods and/or systems for biometric or identifying information can be implemented on a general purpose or special purpose information handling appliance or logic enabled system, such as a laboratory or diagnostic or production system, using a suitable programming language such as Perl, python, Java, C++, C#, Cobol, C, Pascal, Fortran., PLI, LISP, assembly, etc., and any suitable data or formatting specifications, such as HTML, XML, dHTML, TIFF, JPEG, tab-delimited text, binary, etc. In the interest of clarity, not all features of an actual implementation are described in this specification. It will be understood that in the development of any such actual implementation (as in any software development project), numerous implementation-specific decisions must be made to achieve the developers' specific goals and subgoals, such as compliance with system-related and/or business-related constraints, which will vary from one implementation to another. Moreover, it will be appreciated that such a development effort might be complex and time-consuming, but would nevertheless be a routine undertaking of software engineering for those of ordinary skill having the benefit of this disclosure.

Furthermore, it is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

All publications and patent applications mentioned in this specification are herein incorporated by reference to the same extent as if each individual publication or patent application was specifically and individually indicated to be incorporated by reference.

What is claimed is:

1. A computer-implemented method comprising:
using one or more processors programmed with instructions to implement a method comprising:
analyzing a forensic biological data file for meeting quality criteria, the forensic biological data file comprising a short tandem repeat (STR) analysis profile computer file;
determining, based on the analyzing, that the STR analysis profile computer file does not meet quality criteria;
in response to the determining, transmitting notification of a request to a plurality of human forensic evaluators over a communications network, wherein the request is for 1) reviewing the forensic biological data file and 2) delivering a forensic evaluation result comprising feedback about the reviewing of the forensic biological data file;
receiving from one or more of the plurality of human forensic evaluators, over the or another communications network, a response indicating willingness to perform the request;
selecting one or more of the plurality of human forensic evaluators to perform the request based on at least one selection criterion;
providing access to the one or more forensic biological data files, over the or another communications network, to the selected one or more of the plurality of human forensic evaluators; and
receiving from the selected one or more of the plurality of human forensic evaluators, over the or another communications network, the forensic evaluation result.

2. The method of claim 1 wherein:
the forensic evaluation result comprises a revised STR profile computer file or a determination that the original file can or cannot be used for further processing.

3. The method of claim 1 wherein the one or more forensic data files comprise an annotated electropherogram of STR amplicons.

4. The method of claim 1 wherein the one or more forensic data files comprise STR allele calls.

5. The method of claim 1 wherein determining the STR analysis profile computer file does not meet quality criteria is based on the forensic biological data file comprising at least one indication of at least one item failing to pass a confidence threshold for identification.

6. The method of claim 5 wherein the at least one indication is one or more of an off-ladder peak, an allele imbalance, a pull-up, or an out of bin peak.

7. The method of claim 5 wherein the forensic evaluation result comprises a reviewed STR profile computer file with the at least one indication cleared from the STR profile computer file.

8. A non-transitory computer-readable storage medium storing instructions that, upon being executed by one or more processors, performs the method comprising:
analyzing a forensic biological data file for meeting quality criteria, the forensic biological data file comprising a short tandem repeat (STR) analysis profile computer file;
determining, based on the analyzing, the STR analysis profile computer file does not meet quality criteria;

in response to the determining, transmitting notification of a request to a plurality of human forensic evaluators over a communications network, wherein the request is for 1) reviewing the forensic biological data file and 2) delivering a forensic evaluation result comprising feedback about the reviewing of the forensic biological data file;

receiving from one or more of the plurality of human forensic evaluators, over the or another communications network, a response indicating willingness to perform the request;

selecting one or more of the plurality of human forensic evaluators to perform the request based on at least one selection criterion;

providing access to the one or more forensic biological data files, over the or another communications network, to the selected one or more of the plurality of human forensic evaluators; and receiving from the selected one or more of the plurality of human forensic evaluators, over the or another communications network, the forensic evaluation result.

9. The non-transitory computer-readable medium of claim 8, wherein the forensic evaluation result comprises a revised STR profile computer file or a determination that the original file can or cannot be used for further processing.

10. The non-transitory computer-readable medium of claim 9, the method further comprising:

in response to the forensic evaluation result comprising a determination that the original file can or cannot be used for further processing, transmitting a request through the or another communications network, to initiate a reprocessing of a biological sample to produce a new forensic biological data file.

11. The non-transitory computer-readable medium of claim 8, the method further comprising uploading the reviewed STR profile computer file to a forensic database.

12. The non-transitory computer-readable medium of claim 8, wherein the one or more forensic data files comprise STR allele calls.

13. The non-transitory computer-readable medium of claim 8, wherein determining the STR analysis profile computer file does not meet quality criteria is based on the forensic biological data file comprising at least one indication of at least one item failing to pass a confidence threshold for identification.

14. The non-transitory computer-readable medium of claim 13, wherein the at least one indication is one or more of an off-ladder peak, an allele imbalance, a pull-up, or an out of bin peak.

15. The non-transitory computer-readable medium of claim 13, wherein the forensic evaluation result-comprises a reviewed STR profile computer file with the at least one indication cleared from the STR profile computer file.

16. The method of claim 2, further comprising:

in response to the forensic evaluation result comprising a determination that the original file can or cannot be used for further processing, transmitting a request through the or another communications network, to initiate a reprocessing of a biological sample to produce a new forensic biological data file.

17. The method of claim 1, further comprising uploading the reviewed STR profile computer file to a forensic database.

* * * * *

UNITED STATES PATENT AND TRADEMARK OFFICE
CERTIFICATE OF CORRECTION

PATENT NO. : 12,141,884 B2
APPLICATION NO. : 17/500690
DATED : November 12, 2024
INVENTOR(S) : Robert A. Schueren et al.

Page 1 of 1

It is certified that error appears in the above-identified patent and that said Letters Patent is hereby corrected as shown below:

In the Claims

In Column 22, Claim 5, Line 49, delete "is based" and insert -- based --, therefor.

In Column 23, Claim 9, Line 22, delete "computer-readable medium" and insert -- computer-readable storage medium --, therefor.

In Column 23, Claim 10, Line 26, delete "computer-readable medium" and insert -- computer-readable storage medium --, therefor.

In Column 24, Claim 11, Line 1, delete "computer-readable medium" and insert -- computer-readable storage medium --, therefor.

In Column 24, Claim 12, Line 4, delete "computer-readable medium" and insert -- computer-readable storage medium --, therefor.

In Column 24, Claim 13, Line 7, delete "computer-readable medium" and insert -- computer-readable storage medium --, therefor.

In Column 24, Claim 14, Line 14, delete "computer-readable medium" and insert -- computer-readable storage medium --, therefor.

In Column 24, Claim 15, Line 19, delete "result-comprises" and insert -- result comprises --, therefor.

Signed and Sealed this
Twenty-first Day of January, 2025

Coke Morgan Stewart
*Acting Director of the United States Patent and Trademark Office*